US012426827B2

(12) United States Patent
Esteller et al.

(10) Patent No.: US 12,426,827 B2
(45) Date of Patent: Sep. 30, 2025

(54) METHOD AND APPARATUS FOR SEQUENCING SENSING BLOCKS FOR NEUROMODULATION

(71) Applicant: Boston Scientific Neuromodulation Corporation, Valencia, CA (US)

(72) Inventors: Rosana Esteller, Santa Clarita, CA (US); Rafael Carbunaru, Valley Village, CA (US); Adarsh Jayakumar, Valencia, CA (US); Thien Tich Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 481 days.

(21) Appl. No.: 17/733,670

(22) Filed: Apr. 29, 2022

(65) Prior Publication Data

US 2022/0346698 A1    Nov. 3, 2022

Related U.S. Application Data

(60) Provisional application No. 63/183,459, filed on May 3, 2021.

(51) Int. Cl.
  *A61N 1/05* (2006.01)
  *A61B 5/00* (2006.01)
  *A61N 1/36* (2006.01)

(52) U.S. Cl.
  CPC .............. *A61B 5/4076* (2013.01); *A61N 1/05* (2013.01); *A61N 1/36067* (2013.01);
  (Continued)

(58) Field of Classification Search
  None
  See application file for complete search history.

(56) References Cited

U.S. PATENT DOCUMENTS 8,818,524 B2    8/2014  Hahn et al.
10,786,674 B2   9/2020  Wu et al.
(Continued)

FOREIGN PATENT DOCUMENTS

CN    117545416 A       2/2024
EP      3180073 B1      3/2020
WO   WO-2022235506 A1  11/2022

OTHER PUBLICATIONS

"European Application Serial No. 22724196.5, Response filed Jun. 12, 2024 to Communication Pursuant to Rules 161(1) and 162 EPC", 7 pgs.
(Continued)

*Primary Examiner* — Ankit D Tejani
(74) *Attorney, Agent, or Firm* — Schwegman Lundberg & Woessner, P.A.

(57) ABSTRACT

An example of a system for delivering neurostimulation to a patient and controlling the delivery of neurostimulation using sensors may include a stimulation output circuit, a sensing circuit, and a control circuit. The stimulation output circuit may be configured to deliver the neurostimulation. The sensing circuit may be configured to receive sensed signals from the sensors and to process the sensed signals. The sensing circuit has adjustable settings controlling the processing of the sensed signals. The control circuit may be configured to control the delivery of the neurostimulation using the processed sensed signals and to control the settings of the sensing circuit according to a sequence of sensing blocks each including a set of sensing parameters.

20 Claims, 10 Drawing Sheets

(52) U.S. Cl.
CPC ..... *A61N 1/36139* (2013.01); *A61N 1/36185* (2013.01); *A61B 5/0031* (2013.01)

(56) References Cited

U.S. PATENT DOCUMENTS

| | | | |
|---|---|---|---|
| 2013/0345591 A1* | 12/2013 | Hincapie Ordonez | ................ A61B 5/395 600/546 |
| 2019/0001121 A1* | 1/2019 | Lara | ............ A61N 1/36082 |
| 2019/0336026 A1 | 11/2019 | Dawoud et al. | |
| 2019/0388692 A1* | 12/2019 | Dinsmoor | ........ A61N 1/36171 |

OTHER PUBLICATIONS

"International Application Serial No. PCT/US2022/026952, International Preliminary Report on Patentability mailed Nov. 16, 2023", 7 pgs.
"International Application Serial No. PCT/US2022/026952, International Search Report mailed Jul. 28, 2022", 4 pgs.
"International Application Serial No. PCT/US2022/026952, Written Opinion mailed Jul. 28, 2022", 5 pgs.

* cited by examiner

METHOD AND APPARATUS FOR SEQUENCING SENSING BLOCKS FOR NEUROMODULATION

CLAIM OF PRIORITY

This application claims the benefit of priority of U.S. Provisional Patent Application Ser. No. 63/183,459, filed on May 3, 2021, which is herein incorporated by reference in its entirety.

TECHNICAL FIELD

This document relates generally to neurostimulation and more particularly to a neurostimulation system that controls signal sensing spatially and temporally using a programmable sequence of sensing blocks.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical pulses. The delivery is controlled using stimulation parameters that specify spatial (where to stimulate), temporal (when to stimulate), and informational (patterns of pulses directing the nervous system to respond as desired) aspects of a pattern of the electrical pulses. Various signals may be sensed from a patient and/or an environment of the patient for setting and adjusting the stimulation parameters. For example, a signal indicative of the patient's changing condition may be sensed to start, stop, or adjust the delivery of a neurostimulation therapy, and a signal indicative of the patient's response to a neurostimulation therapy may be sensed to allow for closed-loop control of its delivery. Efficacy and safety of such neurostimulation therapies may depend on proper sensing of signals that is controlled using sensing parameters that specify spatial (where to sense), temporal (when to sense), and informational (signal conditioning and processing) aspects of sensing.

SUMMARY

An example (e.g., "Example 1") of a system for delivering neurostimulation to a patient and controlling the delivery of neurostimulation using sensors may include a stimulation output circuit, a sensing circuit, and a control circuit. The stimulation output circuit may be configured to deliver the neurostimulation. The sensing circuit may be configured to receive sensed signals from the sensors and to process the sensed signals. The sensing circuit has adjustable settings controlling the processing of the sensed signals. The control circuit may be configured to control the delivery of the neurostimulation using the processed sensed signals and to control the settings of the sensing circuit according to a sequence of sensing blocks each including a set of sensing parameters.

In Example 2, the subject matter of Example 1 may optionally be configured to include an implantable medical device including the stimulation output circuit, the sensing circuit, and the control circuit.

In Example 3, the subject matter of Example 2 may optionally be configured such that the implantable medical device includes at least one internal sensor of the sensors.

In Example 4, the subject matter of any one or any combination of Examples 2 and 3 may optionally be configured to include at least one external sensor of the sensors. The at least one external sensor is external to and communicatively coupled to the implantable medical device.

In Example 5, the subject matter of Example 4 may optionally be configured such that the at least one external sensor includes an implantable sensor configured to be placed in the patient.

In Example 6, the subject matter of any one or any combination of Examples 4 and 5 may optionally be configured such that the at least one external sensor includes a sensor configured to be externally worn by the patient or to be placed remotely from the patient.

In Example 7, the subject matter of any one or any combination of Examples 2 to 6 may optionally be configured to further include a programming device configured to program the implantable medical device. The programming control circuit includes a programming control circuit and a user interface. The programming control circuit is configured to generate parameters for programming the implantable medical device to control the delivery of the neurostimulation pulses according to the pattern of neurostimulation pulses and to control the settings of the sensing circuit according to the sequence of sensing blocks. The user interface is coupled to the programming control circuit and includes a presentation device, a user input device, and an interface control circuit. The interface control circuit includes a stimulation programming circuit configured to generate the pattern of neurostimulation pulses and a sensing programming circuit configured to generate the sequence of sensing blocks.

In Example 8, the subject matter of Example 7 may optionally be configured to include a sensing composer implemented using the presentation device, the user input device, and the sensing programming circuit, the sensing composer configured to allow for composition of the sequence of sensing blocks to customize the settings for the sensing circuit for at least one of the patient or a therapy using the neurostimulation.

In Example 9, the subject matter of any one or any combination of Examples 2 to 8 may optionally be configured to further include an external device configured to be communicatively coupled to the implantable medical device, to store the processed sensed signals, and to adjust the settings of the sensing circuit using the processed sensed signals.

In Example 10, the subject matter of any one or any combination of Examples 1 to 9 may optionally be configured such that the sensing circuit includes a plurality of individually controllable sensing channels configured to receive and to process two or more signals of the sensed signals simultaneously.

In Example 11, the subject matter of any one or any combination of Examples 1 to 10 may optionally be configured such that the control circuit is configured to store one or more sensing algorithms and the sensing parameters used by each sensing algorithm of the one or more sensing algorithms and to control the settings of the sensing circuit by executing a sensing algorithm selected from the stored one or more algorithms.

In Example 12, the subject matter of Example 11 may optionally be configured such that the control circuit includes a microcontroller unit (MCU) including firmware controlling the settings of the sensing circuit and storing the one or more sensing algorithms each as a stand-alone image.

In Example 13, the subject matter of Example 12 may optionally be configured such that the control circuit further includes registers storing parameters defining the settings of the sensing circuit and is configured to adjust the settings of the sensing circuit without changing the firmware.

In Example 14, the subject matter of any one or any combination of Examples 1 to 13 may optionally be configured such that the control circuit is configured to adjust one or more sensing parameters of the sensing parameters using one or more signals of the processed sensed signals.

In Example 15, the subject matter of any one or any combination of Examples 1 to 14 may optionally be configured such that the control circuit is configured to store adjustable parameters used by the one or more sensing algorithms and to dynamically adjust the adjustable parameters during the delivery of the neurostimulation and the sensing of the signals.

An example (e.g., "Example 16") of a method for delivering neurostimulation is also provided. The method may include delivering the neurostimulation from a stimulation device, receiving sensed signals from sensors and processing the sensed signals using a sensing circuit having adjustable settings controlling the processing of the sensed signals, controlling the delivery of the neurostimulation using the processed sensed signals using a control circuit, and controlling the settings of the sensing circuit according to a sequence of sensing blocks each including a set of sensing parameters using the control circuit.

In Example 17, the subject matter of Example 16 may optionally further include customizing the sequence of sensing blocks for at least one of a patient or a therapy.

In Example 18, the subject matter of customizing the sequence of sensing blocks as found in Example 17 may optionally include customizing each of one or more blocks of the sequence of sensing blocks.

In Example 19, the subject matter of any one or any combination of Examples 16 to 18 may optionally further include adjusting at least one sensing parameter of the set of sensing parameters according to at least one of a schedule or a specified event.

In Example 20, the subject matter of any one or any combination of Examples 16 to 19 may optionally further include adjusting at least one sensing parameter of the set of sensing parameters using one or more signals of the processed sensed signals.

In Example 21, the subject matter of any one or any combination of Examples 16 to 20 may optionally further include dynamically adjusting at least one sensing parameter of the set of sensing parameters during the delivery of the neurostimulation and the sensing of the signals.

In Example 22, the subject matter of receiving the sensed signals from the sensors and processing the sensed signals using the sensing circuit as found in any one or any combination of Examples 16 to 21 may optionally include receiving and processing two or more signals of the sensed signals simultaneously using a plurality of individually controllable sensing channels of the sensing circuit.

In Example 23, the subject matter of any one or any combination of Examples 16 to 22 may optionally further include storing one or more sensing algorithms in the control circuit, and the subject matter of controlling the settings of the sensing circuit as found in any one or any combination of Examples 16 to 22 may optionally include executing a sensing algorithm selected from the stored one or more algorithms.

In Example 24, the subject matter of Example 23 may optionally include executing the sensing algorithm using firmware of a microcontroller of the control circuit and storing the set of sensing parameters in the microcontroller and one or more registers coupled to the microcontroller to allow the settings of the sensing circuit to be adjusted without changing the firmware.

An example (e.g., "Example 25") of a non-transitory computer-readable storage medium is also provided. The non-transitory computer-readable storage medium includes instructions, which when executed by a system, cause the system to perform a method for delivering neurostimulation. The method may include delivering the neurostimulation from a stimulation device, receiving sensed signals from sensors and processing the sensed signals using a sensing circuit having adjustable settings controlling the processing of the sensed signals, controlling the delivery of the neurostimulation using the processed sensed signals using a control circuit, and controlling the settings of the sensing circuit according to a sequence of sensing blocks each including a set of sensing parameters using the control circuit.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
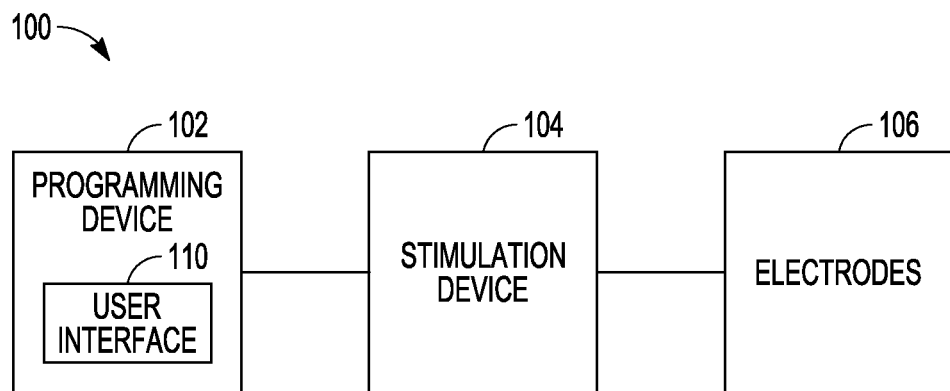
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that can sense various signals, deliver neurostimulation, and controls the delivery of the neurostimulation using the sensed signals. The system can control the sensing of the various signals spatially and temporally using a programmable sequence of sensing blocks and can use the sensed signals to determine and adjust settings for the neurostimulation and settings for the sensing. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device.

A neurostimulation system may sense signals using various types of sensor (e.g., implantable leads with stimulation and sensing electrodes, other implantable sensors, external sensors worn by the patient, external sensors placed in the vicinity of the patient, and percutaneous sensors). Characteristics of a signal and features of interest that can be extracted from the signal to indicate the patient's condition and/or response to the neurostimulation can determine when the signal is to be sensed and how the signal is conditioned (e.g., amplified and/or filtered) and sampled. When being used in certain applications, it can be crucial for the neurostimulation system to sense from different spatial locations at different times. For example, in DBS, to avoid undesirable side effects and ensure desirable clinical effects, there may be different spatial locations that need to be sensed in an internal brain structure within the limbic system to evaluate local field potentials (LFPs), within the basal ganglia to evaluate evoked potentials (EPs) or evoked residential neural activities (ERNA) features, or within neocortical areas of the brain to evaluate motor EPs or motor LFPs signatures. Additionally, different signals have different frequency characteristics, and/or the frequency ranges of interest for different signals may be different, requiring different cutoff frequencies for filtering and hence different sampling frequencies. For example, spinal cord EPs may have a frequency range of 300 Hz-5 kHz, while a bed sensor for sensing the patient's movements on bed may have frequencies below 10 Hz. Thus, there is a need to sense from different sites, at different times, and/or using different cutoff frequencies and sampling rates.

The present subject matter provides for control of sensing of various signals using a sequence of sensing settings, referred to as sensing blocks, each including sensing parameters defining, for example, when and where each signal is sensed and how it is conditioned for further processing before being used to control neurostimulation. A user interface is provided to allow a user to program the sequence of sensing blocks based on the signal being sensed and the features of interest to be extracted from the sensed signal. While the neurostimulation system is discussed as an example in which the sequence of sensing blocks can be used, the present subject matter can be applied to provide spatial and temporal control of sensing settings in any diagnostic and/or therapeutic systems.

In this document, unless noted otherwise, a "patient" includes a person receiving treatment delivered from, and/or monitored using, a neurostimulation system according to the present subject matter, and a "user" includes a physician or other caregiver who examines and/or treats the patient using the neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, stimulation device 104 senses one or more signals and/or receives one or more sensed signals from sensors, and the delivery of the neurostimulation can also be controlled using the sensed signal(s). In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 110 can be configured for SCS applications. While an SCS system is illustrated and discussed as an example, the present subject matter applies to any neurostimulation system with electrodes placed in locations suitable for sensing one or more neural signals from which indications of degenerative and/or other nerve diseases can be detected and monitored.

Figure 2:
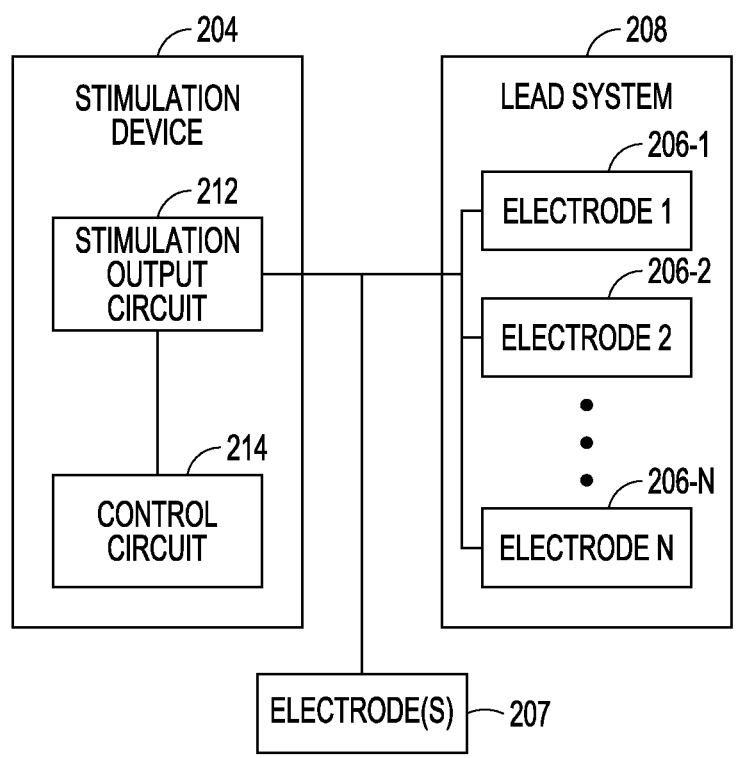
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a control circuit 214. Stimulation output circuit 212 produces and delivers neurostimulation pulses. Control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥1. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none from electrode(s) 207. Multipolar stimulation uses a multipolar electrode configuration with multiple (two or more) electrodes selected from electrodes 206 and optionally electrode(s) 207.

In various embodiments, the number of leads and the number of electrodes on each lead depend on, for example, the distribution of target(s) of the neurostimulation and the need for controlling the distribution of electric field at each target. In various embodiments, lead system 208 can include 2 leads each having 8 electrodes, 4 leads each having 8 electrodes, 2 leads each having 16 electrodes, or any other number of leads and electrodes needed for delivering neurostimulation to identified target(s). Lead and electrode configurations are illustrated in this document as examples and not limitations. For example, various embodiments can use paddle electrodes, cuff electrodes, and other electrodes suitable for delivering neurostimulation.

Figure 3:
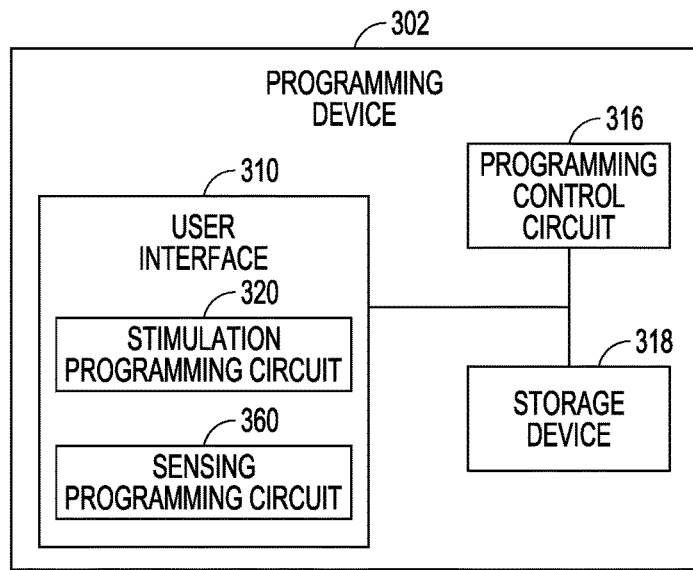
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation programming circuit 320 and a sensing programming circuit 360. Storage device 318 stores information used by programming control circuit 316, stimulation programming circuit 320, and sensing programming circuit 360, such as information about a stimulation device that relates the neurostimulation program to the plurality of stimulation parameters. In various embodiments, stimulation programming circuit 320 and sensing programming circuit 360 can be configured to support functions related to stimulation and sensing, respectively, that allow for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions, including composition of the sequence of sensing blocks, using graphical methods. In this document, "neurostimulation programming" can include the definition of the one or more stimulation waveforms, including the definition of one or more stimulation fields.

In various embodiments, circuits of neurostimulation system 100, including its various embodiments discussed in this document, may be implemented using a combination of hardware and software. For example, the circuit of user interface 110, control circuit 214, programming control circuit 316, stimulation programming circuit 320, and sensing programming circuit 360, including their various embodiments discussed in this document, may be implemented using an application-specific circuit constructed to perform one or more particular functions and/or a general-purpose circuit programmed to perform such function(s). Such a general-purpose circuit can include, but is not limited to, a microprocessor or a portion thereof, a microcontroller or portions thereof, and/or a programmable logic circuit or a portion thereof.

Figure 4:
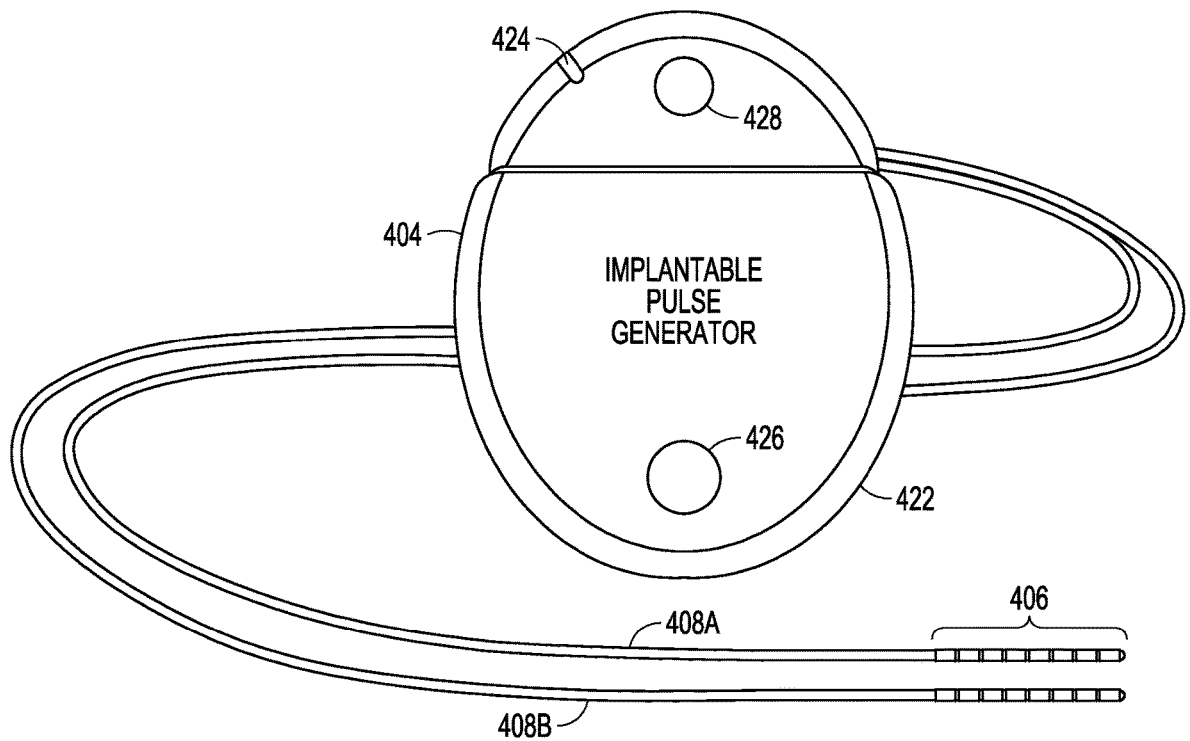
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 4, leads 408A and 408B each include 8 electrodes 406 at the distal end. The number and arrangement of leads 408A and 408B and electrodes 406 as shown in FIG. 4 are only an example, and other numbers and arrangements are possible. In various embodiments, the electrodes are ring electrodes. In various embodiments applying DBS or SCS, the implantable leads and electrodes may be configured by shape and size to provide electrical neurostimulation energy to a neuronal target included in the patient's brain or configured to provide electrical neurostimulation energy to target nerve cells in the patient's spinal cord.

Figure 5:
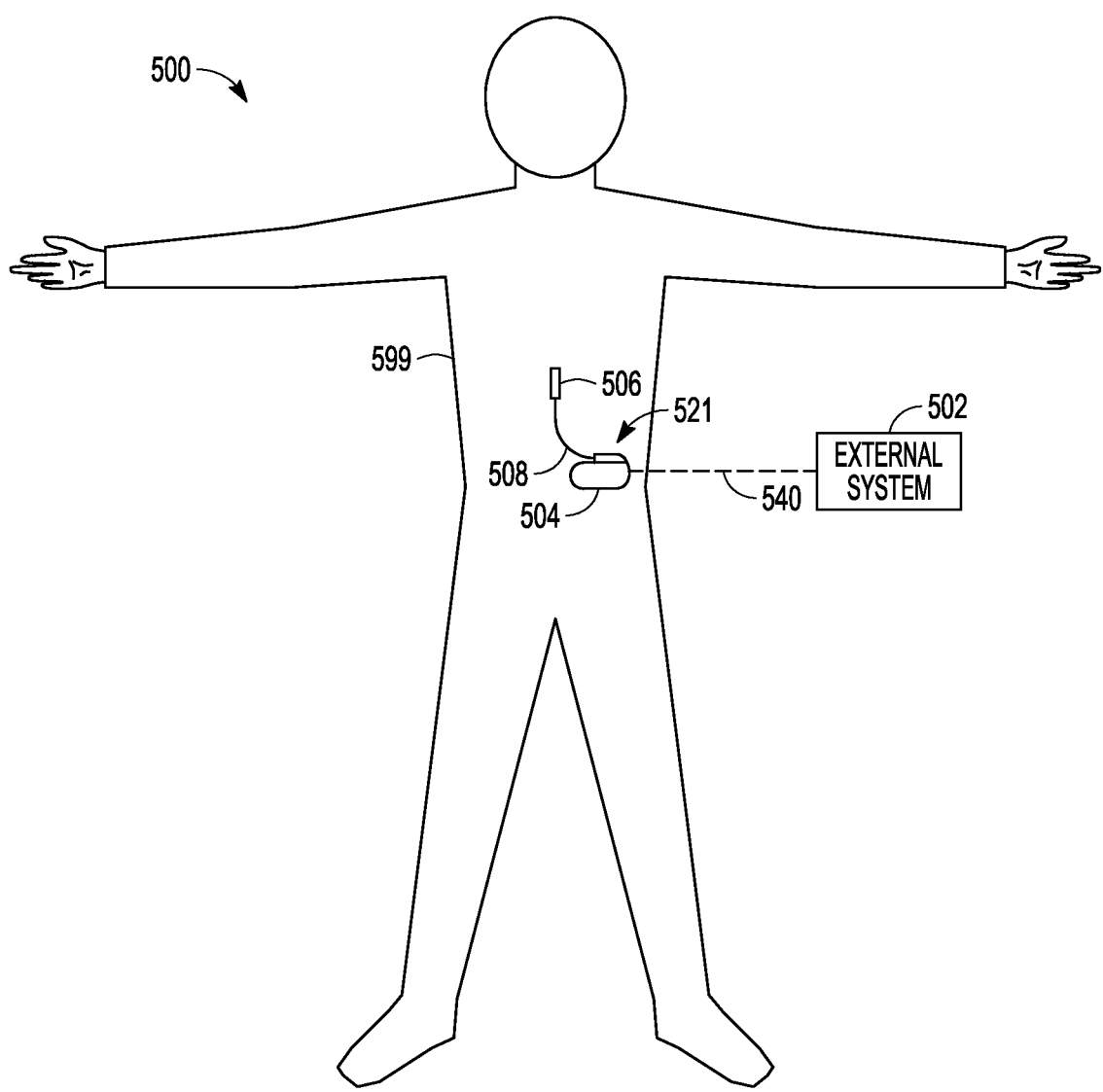
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external system 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and shapes of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
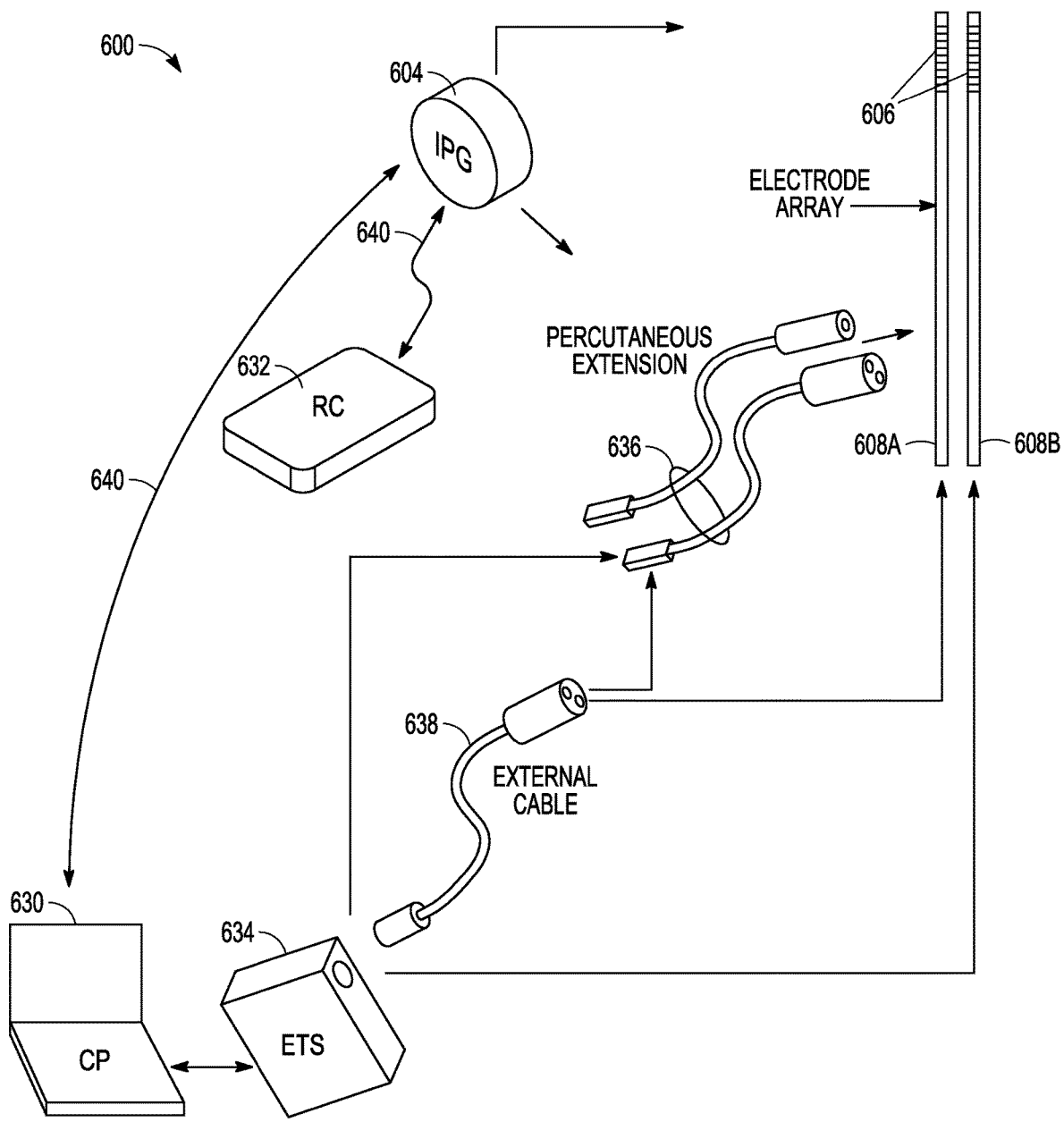
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 604 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device configured for ambulatory use and may be used as a preliminary stimulator after leads 408A and 408B have been implanted and used prior to stimulation with IPG 604 to test the patient's responsiveness to the stimulation that is to be provided by IPG 604. ETS 634 may include cable connectors allowing it to readily interface the proximal end of external leads that are chronic use and may include replaceable batteries.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=$\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 640. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
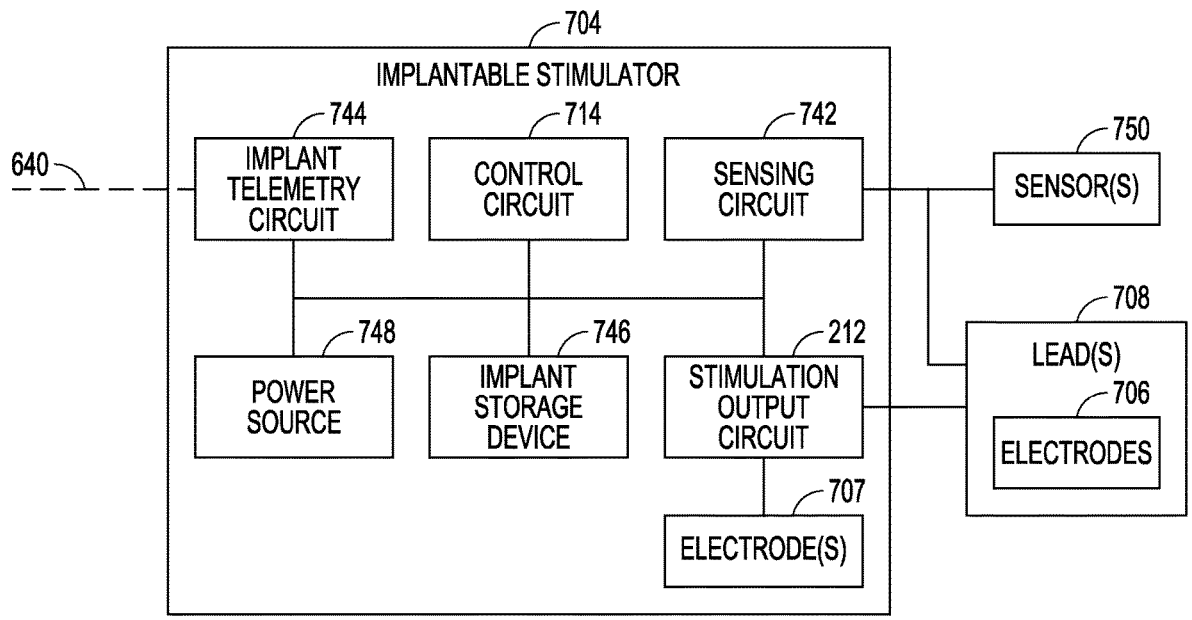
FIG. 7 illustrates an embodiment of an implantable stimulator, one or more leads, and one or more sensors of a neurostimulation system, such as the neurostimulation system of FIG. 6.

FIG. 7 illustrates an embodiment of implantable stimulator 704, one or more leads 708, and one or more sensor(s) 750 of a neurostimulation system, such as system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a control circuit 714, an implant storage device 746, an implant telemetry circuit 744, a power source 748, and one or more electrodes 707. Sensing circuit 742 senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation (e.g., signals discussed below with reference to FIG. 10). In various embodiments, sensing circuit 742 senses one or more neural signals using at least electrodes 706 and receives one or more signals sensed by sensor(s) 750. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Control circuit 714 represents an example of control circuit 214 and controls the delivery of the neurostimulation pulses using the plurality of stimulation parameters specifying the pattern of neurostimulation pulses. In various embodiments, control circuit 714 controls the delivery of the neurostimulation pulses using the one or more sensed signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4. Sensor(s) 750 sense(s) one or more signals used for controlling the neurostimulation. In various embodiments, sensor(s) 750 can be included in implantable stimulator 704, implantable in the patient separately from implantable stimulator 704, externally worn by the patient, and/or remote from the patient, as further discussed below with reference to FIG. 10.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 (e.g., by installing a new application in a smart device such as a smartphone) and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), any of the physiological sensed data or features extracted from the sensed data, and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
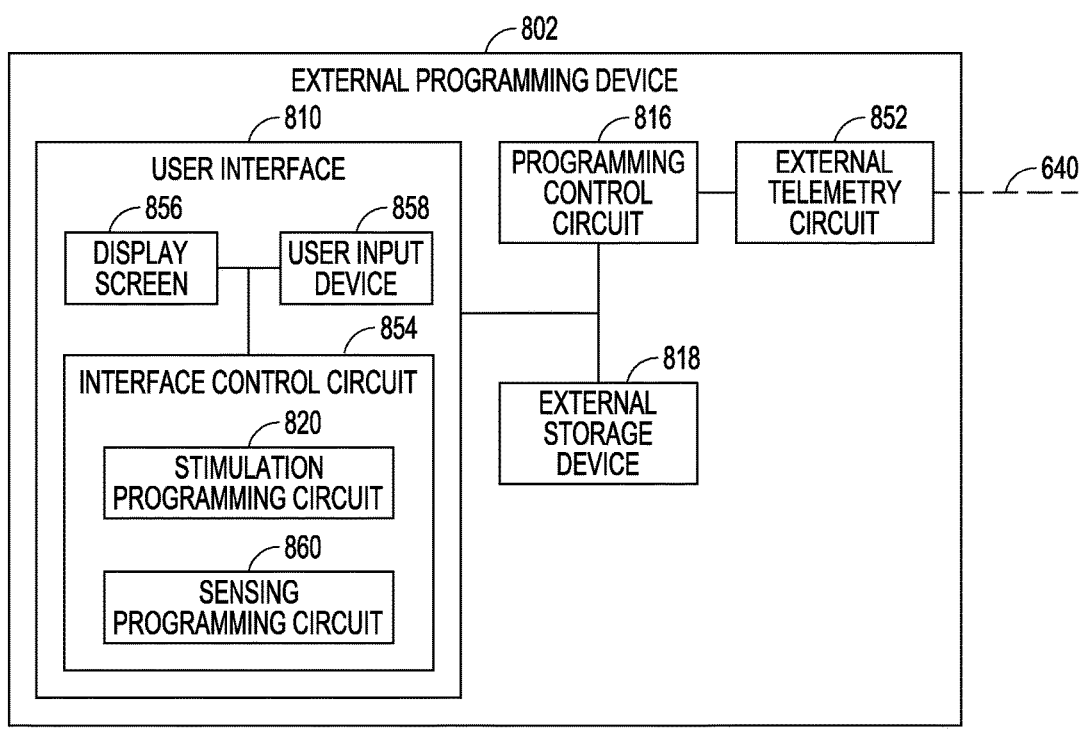
FIG. 8 illustrates an embodiment of an external programming device of a neurostimulation system, such as the neurostimulation system of FIG. 6.

FIG. 8 illustrates an embodiment of an external programming device 802 of a neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS or SCS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g., mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316. Programming control circuit 816 generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). Programming control circuit 816 also generates a plurality of sensing parameters, which is to be transmitted to implantable stimulator 704, based on a sensing configuration, such as a sequence of sensing blocks. The neurostimulation program and sensing configuration may be created and/or adjusted by the user using user interface 810 and stored in external storage device 818. In various embodiments, programming control circuit 816 can check values of the plurality of stimulation parameters and/or the plurality of sensing parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 can include stimulation programming circuit 820 and a sensing programming circuit 860. Stimulation programming circuit 820 allows for composition of the neurostimulation program or the pattern of neurostimulation pulses according to which the neurostimulation is delivered. Sensing programming circuit 860 allows for composition of the sensing configuration, such as the sequence of sensing blocks, according to which the signals are sensed to be used in controlling the delivery of the neurostimulation, as further discussed below with reference to FIGS. 9-15.

In various embodiments, external programming device 802 can have operation modes including a composition mode (during which the sequence of sensing blocks and/or the pattern of neurostimulation pulses are composed) and a real-time programming mode. Under the composition mode, user interface 810 is activated, while programming control circuit 816 is temporarily deactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704. In various embodiments, the delivery of the neurostimulation is controlled using a closed-loop system with programming control circuit 816 operating in the real-time programming mode, under which both user interface 810 and programing control circuit 816 are activated. Programming control circuit 816 dynamically updates values of the plurality of stimulation parameters in response to changes in one or more sensing algorithms (e.g., programmed in control circuit 714) that follows the sequence of sensing blocks and transmits the plurality of stimulation parameters with the updated values to implantable stimulator 704.

Figure 9:
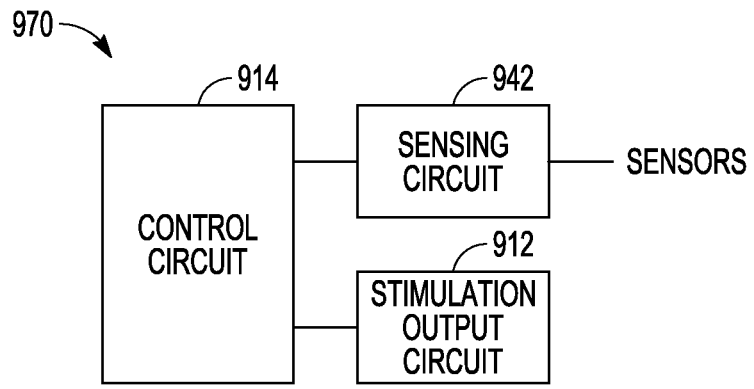
FIG. 9 illustrates an embodiment of a system for delivering neurostimulation and controlling the delivery of neurostimulation using sensors.

FIG. 9 illustrates an embodiment of a system 970 for delivering neurostimulation and controlling the delivery of neurostimulation using sensors. System 970 includes a stimulation output circuit 912, a sensing circuit 942, and a control circuit 914. Stimulation output circuit 912 can deliver the neurostimulation. Sensing circuit 942 can receive sensed signals from sensors and process the sensed signals. Settings of sensing circuit 942 that control the processing of the sensed signals are adjustable. Control circuit 914 can control the delivery of the neurostimulation using the processed sensed signals and control the settings of sensing circuit 942 according to a sequence of sensing blocks each including a set of sensing parameters.

System 970 can be implemented in neurostimulation systems such as systems 100, 500, and 600. In various embodiments, system 970 is implemented in an implantable medical device, such as IPG 404, IPG or implantable stimulator 504, IPG 604, or implantable stimulator 704 as discussed in this document. For example, when system 970 is implemented in implantable stimulator 704, stimulation output circuit 212 can be configured to include stimulation circuit 912, sensing circuit 742 can be configured to include sensing circuit 942, and control circuit 714 can be configured to include control circuit 914. The sensors can include any combination of sensor(s) 750, electrodes 706, and electrode(s) 707.

In various embodiments, the neurostimulation is delivered in the form of electrical stimulation pulses (referred to as neurostimulation pulses in this document), and system 970 is configured for delivering the neurostimulation pulses and controlling the delivery of the neurostimulation pulses using signals sensed using the sensors. Stimulation output circuit 912 (also referred to as "stimulation hardware") can deliver neurostimulation pulses. Sensing circuit 942 (also referred to as "sensing hardware") can receive the sensed signals from the sensors and process the sensed signals for the controlling of the delivery of the neurostimulation pulses in various direct and/or indirect manners (e.g., directly by adjusting the delivery of the neurostimulation pulses automatically in response to a detected change in a sensed signal, or indirectly by notifying the user about a patient control change detected from a sensed signal to allow the user to decide that the delivery of the neurostimulation pulses should be adjusted). Sensing circuit 942 includes a plurality of sensing channels that allow for receiving and processing a plurality of signals simultaneously. Sensing circuit 942 has adjustable settings controlling the processing of the sensed signals. The processing of each received sensed signal can include, for example, one or more of:

amplification of the sensed signal;
    filtering of the sensed signal;
    digitization of the sensed signal;
    averaging of the sensed signal; and
    extracting one or more features from the sensed signal.

In some embodiments, the settings of sensing circuit 942 can also be adjusted to control operation of one or more of the sensors, such as to activate and deactivate a sensor and/or to adjust sensor parameters of the sensor according the when and how that sensor is used. Control circuit 914 can control the delivery of the neurostimulation pulses according to a pattern of stimulation pulses and using the sensed signals received and processed by sensing circuit 942. In various embodiments, control circuit 914 controls the delivery of the neurostimulation pulses executing a stimulation algorithm that uses stimulation parameters and adjusts the stimulation parameters using the sensed signals received and processed by sensing circuit 942. Control circuit 914 can also control the settings of sensing circuit 942 according to a sequence of sensing blocks each including a set of sensing parameters. In various embodiments, control circuit 914 controls the settings of sensing circuit 942 by executing a sensing algorithm using sensing parameters defining the sensing blocks. Control circuit 914 can store one or more sensing algorithms and the sensing parameters used by each sensing algorithm of the one or more sensing algorithms.

Figure 10:
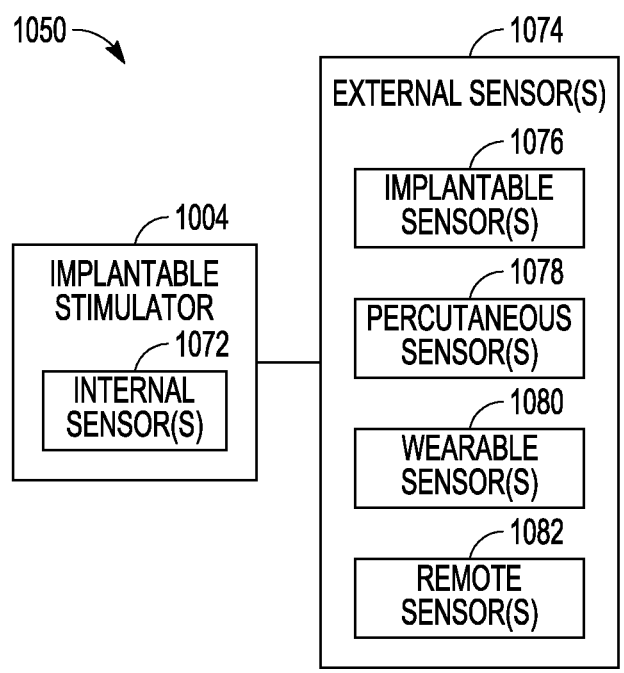
FIG. 10 illustrates an embodiment of sensors that can be used by a neurostimulation system, such as the system of FIG. 9.

FIG. 10 illustrates an embodiment of sensors 1050 that can be used by a neurostimulation system, such as system 970. In various embodiments, sensing circuit 942 can receive signals from sensors 1050.

Sensors 1050 can include one or more internal sensors 1072 and/or one or more external sensor(s) 1074. Internal sensor(s) 1072 is(are) included in an implantable medical device 1004. Examples for implantable stimulator 1004 include IPG 404, IPG or implantable stimulator 504, IPG 604, or implantable stimulator 704 as discussed in this document. External sensor(s) 1074 is(are) external to and communicatively coupled to implantable stimulator 1004. In various embodiments, external sensor(s) 1074 can include one or more implantable sensors 1076, one or more percutaneous sensors 1078, one or more wearable sensors 1080, and/or one or more remote sensors 1082. Each of external sensor(s) 1074 is communicatively coupled to implantable stimulator 1004 via a wired or wireless connection. Implantable sensor(s) 1076 can be placed within the patient in whom implantable stimulator 1004 is placed. Percutaneous sensor(s) 1078 can be partially inserted into the patient. Wearable sensor(s) 1080 can be externally worn by the patients, such as attached to the patient's skin or otherwise carried by the patient to move with the patient. Remote sensor(s) 1082 can sense signals from the patient or an environment without being carried by or moving with the patient. Choice of a type of external sensor for sensing a desirable signal can depend on the nature of the signal and available sensor technology. Examples of sensors 1050 include:

- electrodes to sense neural electric signals (e.g., electrodes on one or more implantable leads coupled to the implantable medical device and electrodes incorporated onto the implantable medical device, such as electrodes 706 and electrode(s) 707);
- motion sensors in different body parts of the patient to sense motion signals;
- electrocardiographic (ECG) sensors to sense ECG signals;
- a heart rate sensor to sense a signal from which the patient's heart rate can be detected;
- a blood pressure sensor to sense a signal indicative of the patient's blood pressure;
- an impedance sensor to sense a skin impedance;
- a sleep sensor to sense a signal indicative of a sleep state (e.g., sleep stage) of the patient or a signal indicative of a total time of resting or sleeping;
- a chemical sensor to sense a level or sugar or other substance (e.g., in a blood vessel of the patient);
- an oximeter to sense oxygen saturation of the patient;
- a screen writing sensor with which the patient is to follow a figure or letters in a screen to sense hand tremor, bradykinesia, or muscle twitches while writing (micrographia);
- a respiration sensor to sense a signal indicative of respiratory cycles of the patient;
- an acoustic sensor to sense an acoustic signal (e.g., an echo-Doppler sensor to sense a blood flow in the patient);
- an eye sensor to sense a pupil dilation of the patient;
- a bed sensor to sense movements of the patient on a bed (e.g., a pad sensor)
- a step counter to count steps of walking of the patient; and
- an activity sensor to sense an activity level of the patient.

Each of these sensors can be configured to be an implantable sensor, a percutaneous sensor, a wearable sensor, or a remote sensor, depending on the physiological and design considerations (e.g., best sites for sensing desirable signals, least invasive or most convenient way for placing the sensors, and sensor types that are already available for sensing the desirable signals). In various embodiments, sensors 1050 can include any sensors selected from these examples as well as other sensors that can be used to control the neurostimulation.

Figure 11:
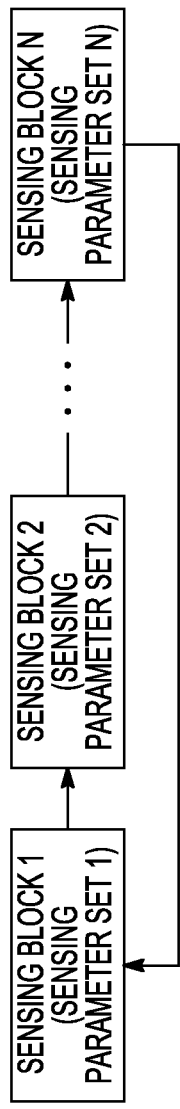
FIG. 11 illustrates an embodiment of a sequence of sensing blocks that can be used in a neurostimulation system, such as the system of FIG. 9.

FIG. 11 illustrates an embodiment of a sequence of sensing blocks according to which settings of a sensing circuit in a neurostimulation system, such as the settings of sensing circuit 942 in system 970, can be controlled. The sequence of sensing blocks can include two or more sensing blocks each including a set of sensing parameters. In the illustrated embodiment, the sequence of sensing blocks includes Sensing Block 1 (including Sensing Parameter Set 1), Sensing Block 2 (including Sensing Parameter Set 2), . . . , Sensing Block N (including Sensing Parameter Set N). In various embodiments, the sequence of sensing blocks is customizable for a therapy and/or for the patient. The customization can include customizing the set of sensing parameters for each block of the sequence of sensing blocks and/or customizing the order of the sensing blocks in the sequence. The sensing parameters can each have values variable across different sensing blocks and/or variable within a sensing block. The sequence of sensing blocks can include one or more no-sensing blocks for which the sensing of the signals is suspended. In various embodiments, the sensing circuit can cycle through Sensing Blocks 1 to N continuously, periodically, according to a specified schedule, when neurostimulation is being delivered, or in response to a specified event or condition.

The sensing parameters in each sensing block of the sequence of sensing blocks can specify one or more of the following, for example:

- one or more sensors to activate (i.e., signals to be sensed) for the sensing block;
- one or more sensing channels to activate for the sensing block;
- sensing electrodes for each sensing channel;
- sampling frequency for each sensed signal (depending on the type of the signal);
- filter type and cutoff frequencies for each sensed signal (depending on the type of the signal);
- sensing time window for each sensed signal (duration of sensing, depending on the signal and the signal features of interest, e.g., response following a stimulus);
- whether each sensed signal is averaged (e.g., responses averaged for multiple stimuli);
- whether each sensed signal or one or more signal features extracted from that signal is/are stored (e.g., whether to store a neural signal including an ECAP, an EP (evoked potential), an ERNA (evoked resonant neural activity), and/or an LFP (local field potential), and or to store amplitude(s) of the ECAP, EP, ERNA, and/or LFP);
- type(s) of signal feature to be extracted from each sensed signal (e.g., range, curve length (CL), area under curve (AUC), and/or frequency domain features such as LFPs related to specific frequency bands);

stimulation delivered for purpose of sensing;
default settings for different signals such as EPs, ERNAs, and/or LFPs;
a closed-loop sensing algorithm;
one or more closed-loop parameters (each adjusted using closed-loop sensing control) used within algorithm; and
logic blocks for scheduled sensing (e.g., sensing parameters adjusted according to a schedule) and/or conditional sensing (e.g., sensing parameters adjusted in response to a condition or event).

Different parameters can be specified for processing different types of signals sensed during each sensing block. Examples of controlling various settings of the sensing circuit by specifying sensing parameters in each sensing block include:
programming analog and/or digital filters;
decomposing a sensed signal into frequency components (f or s domain) or another type of signal (e.g., wavelets);
for wavelet kinds of analysis, programming the system to use traditional sets or to allow the user to specify patterns to correlate the signal to the desired patterns;
allowing the user to define and apply filters to a sensed signal in the time domain or other domain (e.g., frequency or wavelets) for phase decomposition, cross-correlation across different channels, phase-amplitude coherence analysis across channels;
defining signal features to be extracted from a sensed signal by power, a change from baseline characteristics, information theory features such as entropy, spectral entropy, mutual information, fractal dimension, etc.;
programming processing of a sensed signal to modulate the sensed signal with another sensed signal (e.g., by addition, subtraction, or multiplication);
using signal features on a sensed signal to control the processing of another sensed signal (e.g., a parameter measured from a sensed signal can trigger sampling and/or filtering of another sensed signal, or can be used to set a cutoff frequency for filtering the other sensed signal);
setting one or more sensing parameters of a sensing block based on one or more sensing parameters of a preceding sensing block.

In various embodiments, types of the sensing parameters that can be specified in each sensing block depend on which settings of the sensing circuit are adjustable, and types of the sensing parameters that are actually specified depend on the types of signals to be sensed and types of information to be obtained from the sensed signals.

Figure 12:
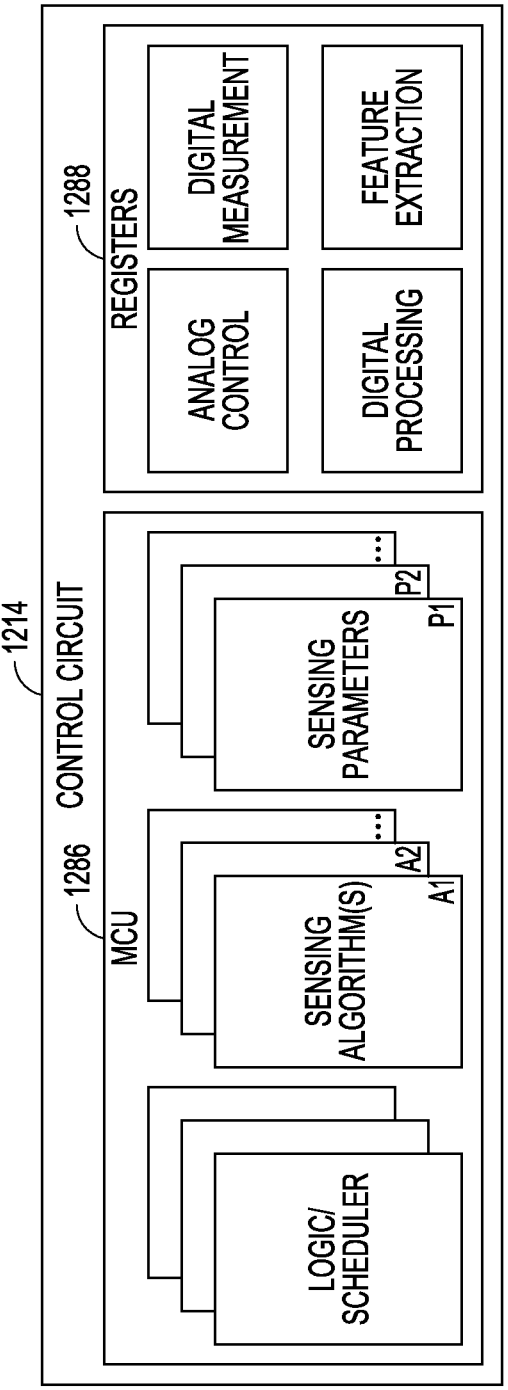
FIG. 12 illustrates an embodiment of a control circuit of a neurostimulation system, such as the system of FIG. 9.

FIG. 12 illustrates an embodiment of a control circuit 1214 of a neurostimulation system, such as system 970. Control circuit 1214 can represent an example of control circuit 914. In the illustrated embodiment, control circuit 1214 includes a microcontroller unit (MCU) 1286 and registers 1288. MCU 1286 includes one or more central processor units (CPUs), a memory, and programmable input/output peripherals.

When system 970 with control circuit 1214 is implemented in an implantable medical device such as IPG 404, IPG or implantable stimulator 504, IPG 604, or implantable stimulator 704, MCU 1286 includes firmware controlling operations of the implantable medical device including the settings of sensing circuit 942. MCU 1286 can be configured for neurostimulation, including the delivery of the neurostimulation pulses and the settings of sensing circuit 942. Memory of MCU 1286 can store one or more stimulation algorithms controlling the delivery of the neurostimulation and the one or more sensing algorithms controlling the settings of sensing circuit 942. The one or more sensing algorithms can each be loaded into the memory as a stand-alone image and can each be stored in an external flash memory as the stand-alone image (e.g., for transport and programming purposes). The one or more sensing algorithms can each be loaded without requiring a full firmware upgrade of MCU 1286 (e.g., by updating a particular firmware image rather than the entire firmware). The memory of MCU 1286 can also store adjustable parameters used by the one or more stimulation algorithms and the one or more sensing algorithms. In various embodiments, the adjustable parameters are dynamically adjustable during the delivery of the neurostimulation and sensing of the signals (using an external programming device such as CP 630, RC 632, or external programming device 802). In various embodiments, the adjustable parameters are adjustable to allow for change of closed-loop behavior of a stored sensing algorithm without updating the firmware or loading a new sensing algorithm. The settings of sensing circuit 942 are adjustable during the sensing of the signals by adjusting parameters without changing the firmware. In various embodiments, use of the sequenced sensing blocks according to the present subject matter encourages development of generalizable closed-loop sensing algorithms for greatest flexibility, with logic blocks for scheduled and/or conditional sensing executable in MCU 1286.

Registers 1288 can store additional information used by the one or more sensing algorithms stored and executable in MCU 1286. In one embodiment, registers 1288 are implemented in an application-specific integrated circuit (ASIC) and referred to as ASIC registers. In one embodiment, hardware-specific sensing configurations are written into registers 1288. Examples of the hardware-specific sensing configurations include settings for analog control (e.g., which electrodes are used), digital measurement (e.g., when is sensing triggered, sampling frequency), digital processing (i.e., how is the raw data processed, e.g., filtering/averaging), and feature extraction (e.g., which feature(s) is(are) extracted and how each is detected).

Figure 13:
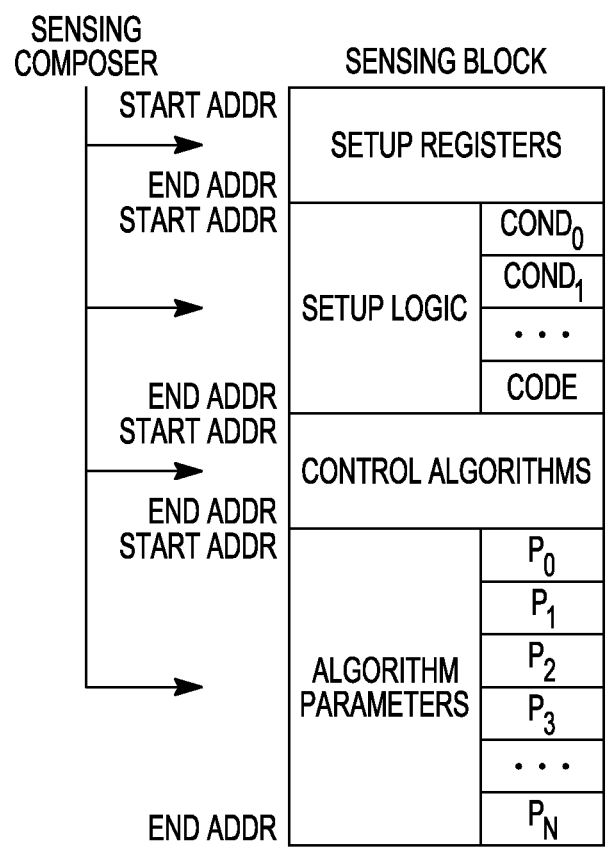
FIG. 13 illustrates an embodiment of a firmware architecture of the control circuit of FIG. 12.

FIG. 13 illustrates an embodiment of a firmware architecture of control circuit 1214. The hardware architecture allows for upgrade of a firmware image, instead of the entire firmware, to add or modify a sensing algorithm. Sensing parameters used by each sensing algorithm can be adjusted during the sensing of the signals without changing the firmware. In various embodiments, the sequence of sensing blocks can be programmed using a sensing composer at software level, without changing the firmware. When control circuit 1214 is part of an implantable medical device, an external device for programming the implantable medical device can be configured to include the sensing composer.

The illustrated firmware architecture, shown by way of example but not by way of restriction, includes the following blocks for controlling the settings of a sensing circuit such as sensing circuit 942:

Setup Registers: the registers are set up for analog control (e.g., which electrodes are used), digital measurement (e.g., when is sensing triggered), digital processing (e.g., how the sensing signals are filtered), and feature extraction (e.g., which feature(s) is(are) extracted from the sensed signals).

Setup Logic: a sensing algorithm is selected, and sensing is performed, based on conditions (e.g., $Cond_0$: select algorithm, $Cond_1$: repeat M times, $Cond_3$: scheduled time to run algorithm, . . . ).

Control Algorithms: the firmware jumps to hard-coded algorithm start address, and parameters of the algorithm are used via pointers.

Algorithm Parameters: parameters are agnostic to the algorithm being executed, while the algorithm knows which parameters to use.

Referring back to FIG. 8, in one embodiment, external programming device 802 is configured to allow for composition of a sensing algorithm for sequencing sensing blocks. Programming control circuit 816 can be configured to generate parameters for programming an implantable medical device, such as implantable stimulator 704, to control the delivery of the neurostimulation pulses according to the pattern of neurostimulation pulses and to control the settings of the sensing circuit, such as sensing circuit 742, according to a sequence of sensing blocks. User interface 810 can be configured to generate the sequence of sensing blocks. In one embodiment, a sensing composer is implemented in external programming device 802 using display screen 856, user input device 858, and sensing programming circuit 860. The sensing composer allows for composition of each sensing block and use of the sensing blocks to create patient- and/or therapy-specific settings for the sensing circuit. Sensing programming circuit 860 can display a sensing composition window or field on display screen 856 and receive user input related to the composition using user input device 858. User interface 810 can include a GUI configured as part of the sensing composer to allow the user to graphically creating and/or editing the sequence of sensing blocks, including creating and/or editing each sensing block individually. In various embodiments, the sensing composer can allow the user to program, for example:

Logic: signal conditioning and sensing scheduling capabilities;

Analog Control: electrodes used for sensing;

Digital measurement: events or conditions that triggers sensing of a signal;

Digital filtering: filtering parameters for each sensed signal;

Feature extraction: signal features to be extracted from each sensed signal; and Control Algorithms: sensing algorithms to be selected.

Figure 14:
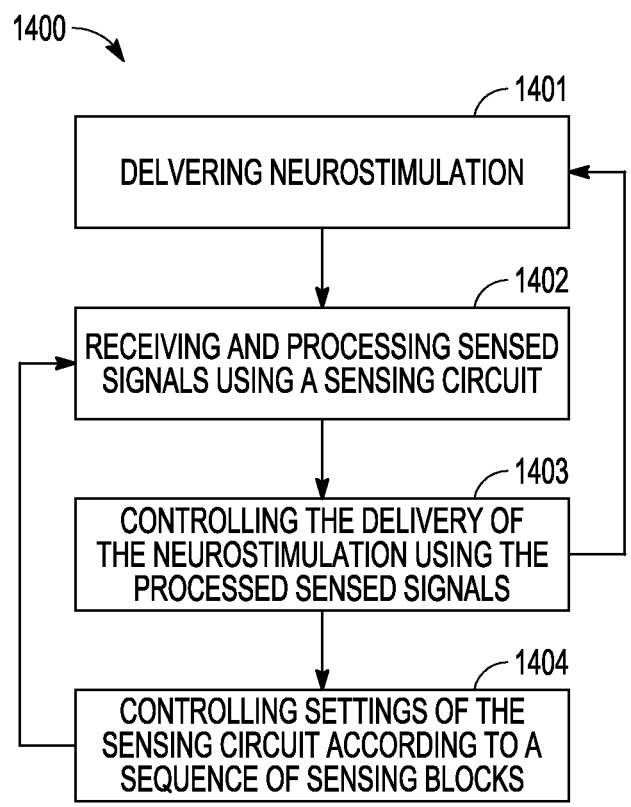
FIG. 14 illustrates an embodiment of a method for delivering neurostimulation and controlling the delivery of neurostimulation using sensors.

FIG. 14 illustrates an embodiment of a method 1400 for delivering neurostimulation and controlling the delivery of neurostimulation using sensors. In one embodiment, method 1400 is performed using system 970.

At 1401, the neurostimulation is delivered from a stimulation device. The neurostimulation can be in the form of electrical pulses. The stimulation device can be an implantable neurostimulator.

At 1402, sensed signals are received and processed using a sensing circuit. The sensing circuit has adjustable settings controlling the processing of the sensed signals. In various embodiments, two or more of the sensed signals are simultaneously received and processed using a plurality of individually controllable sensing channels of the sensing circuit.

At 1403, the delivery of the neurostimulation is controlled using the processed sensed signals using a control circuit. In various embodiments, a closed-loop control algorithm is executed in the control circuit using the processed sensed signals as input.

At 1404, the settings of the sensing circuit are controlled according to a sequence of sensing blocks using the control circuit. The sensing blocks each include a set of sensing parameters. In various embodiments, the sequence of sensing blocks is customized for a patient and/or a therapy. The customization of the sequence of sensing blocks can include customizing each of one or more blocks of the sequence of sensing blocks. In various embodiments, one or more sensing parameters of each sensing block can be adjusted according to a schedule and/or an event or condition. In various embodiments, one or more sensing parameters of each sensing block can be adjusted using one or more signals of the processed sensed signals. In various embodiments, one or more sensing parameters of each sensing block can be dynamically adjusted during the delivery of the neurostimulation and/or the sensing of the signals. In various embodiments, one or more sensing algorithms are stored in the control circuit, and the settings of the sensing circuit is controlled by executing a sensing algorithm selected from the stored one or more algorithms. The sensing algorithm can be executed using firmware of a microcontroller of the control circuit. The sensing parameters can be stored in the microcontroller and one or more registers coupled to the microcontroller to allow the settings of the sensing circuit to be adjusted without changing the firmware.

Figure 15:
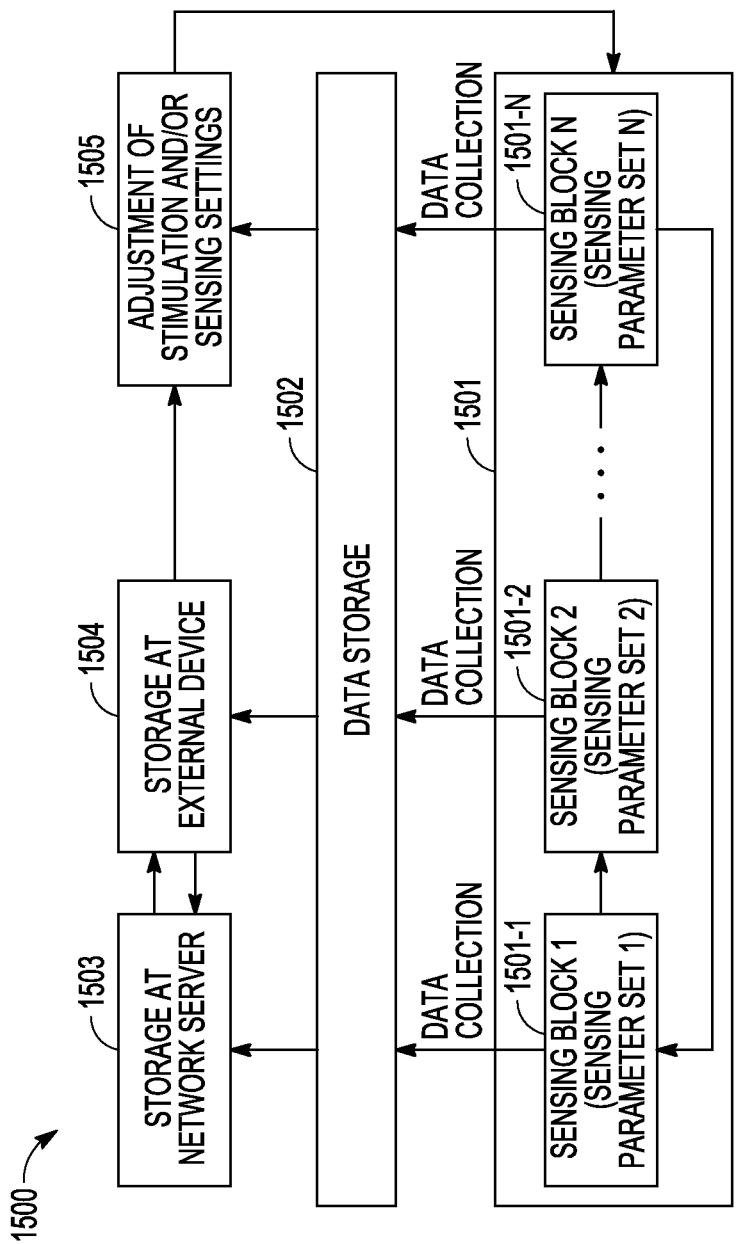
FIG. 15 illustrates an embodiment of a method for data storage and adjustment of stimulation and/or sensing settings associated with sequenced sensing blocks.

FIG. 15 illustrates an embodiment of a method 1500 for data storage and adjustment of stimulation and/or sensing settings associated with sequenced sensing blocks. In one embodiment, method 1500 is performed using system 970 when system 970 is implemented in an implantable medical device (e.g., such as IPG 404, IPG or implantable stimulator 504, IPG 604, or implantable stimulator 704) that is communicatively coupled to an external device (e.g., CP 630, RC 632, external programming device 802, or a generic device with a neurostimulation application installed) and communicatively coupled to a network server. The generic device can be a smartphone, a tablet computer, a laptop computer, or any device that can be configured for storage of sensing data representing the processed sensed signals and control of the settings of the sensing circuit including adjustment of the settings using the sensing data. In various embodiments, the implantable medical device, the external device, and the network server can each store portions of the sensing data.

At 1501, sensing of signals is performed by cycling through a sequence of sensing blocks that includes Sensing Blocks 1 through N, where N≥2. According to the sequence of sensing blocks, sensing of signals is performed at 1501-1 using Sensing Parameter Set 1, at 1501-2 using Sensing Parameter Set 2, . . . and at 1501-N using Sensing Parameter Set N. In some embodiments, one or more parameters of each sensing parameter set can be determined based on one or more parameters of another sensing parameter set (e.g., one or more parameters of Sensing Parameter Set N can be expressed as a function of one or more parameters of Sensing Parameter Set N−1, i.e., Sensing Parameter Set N=f(Sensing Parameter Set N−1), for N=1, 2, . . . ). Sensing data are collected and stored at 1502 as the sensed signals are processed. Portions of the sensing data can be stored in the implantable medical device, transmitted to and stored in the network server at 1503, and/or transmitted to and stored in the external device at 1504. The stimulation and/or sensing settings can be adjusted at 1505 using the sensing data. In various embodiments, the adjustment can be determined within the implantable medical device, the network server, and/or the external device, depending on how each of these devices are configured for sensing control. This allows for closed-loop control of the delivery of the neurostimulation and/or closed-loop control of the sensing of signals.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to a patient and controlling the delivery of the neurostimulation using sensors, the system comprising:
   a stimulation output circuit configured to deliver the neurostimulation;
   a sensing circuit configured to receive sensed signals from the sensors and to process the sensed signals, the sensing circuit having adjustable settings controlling the processing of the sensed signals; and
   a control circuit configured to control the delivery of the neurostimulation using the processed sensed signals and to control the settings of the sensing circuit for receiving the sensed signals from different sensors selected from the sensors for different times according to a precomposed sequence of sensing blocks each including a set of sensing parameters specifying a sensor to be used for sensing each signal of the sensed signals and a sampling frequency to be used for sensing the each signal, the set of sensing parameters programmable for each sensing block of the sequence of sensing blocks for adjusting the settings of the sensing circuit for that sensing block.

2. The system of claim 1, comprising an implantable medical device including the stimulation output circuit, the sensing circuit, and the control circuit.

3. The system of claim 2, wherein the implantable medical device comprises at least one internal sensor of the sensors.

4. The system of claim 2, comprising at least one external sensor of the sensors, the at least one external sensor being external to and communicatively coupled to the implantable medical device.

5. The system of claim 2, further comprising a programming device configured to program the implantable medical device, the programming device including:
   a programming control circuit configured to generate parameters for programming the implantable medical device to control the delivery of the neurostimulation according to a pattern of neurostimulation pulses and to control the settings of the sensing circuit according to the sequence of sensing blocks; and
   a user interface coupled to the programming control circuit and including:
   a presentation device;
   a user input device; and
   an interface control circuit including a stimulation programming circuit configured to generate the pattern of neurostimulation pulses and a sensing programming circuit configured to generate the sequence of sensing blocks.

6. The system of claim 5, wherein the presentation device, the user input device, and the sensing programming circuit are configured to allow for composition of the sequence of sensing blocks to customize the settings for the sensing circuit for at least one of the patient or a therapy using the neurostimulation.

7. The system of claim 2, further comprising an external device configured to be communicatively coupled to the implantable medical device, to store the processed sensed signals, and to adjust the settings of the sensing circuit using the processed sensed signals.

8. The system of claim 1, wherein the control circuit is configured to store one or more sensing algorithms and the sensing parameters used by each sensing algorithm of the one or more sensing algorithms and to control the settings of the sensing circuit by executing a sensing algorithm selected from the stored one or more algorithms.

9. The system of claim 8, wherein the control circuit comprises a microcontroller unit (MCU) including firmware controlling the settings of the sensing circuit and storing the one or more sensing algorithms each as a stand-alone image.

10. The system of claim 8, wherein the control circuit is configured to adjust one or more sensing parameters of the sensing parameters using one or more signals of the processed sensed signals, to store adjustable parameters used by the one or more sensing algorithms, and to dynamically adjust the adjustable parameters during the delivery of the neurostimulation and the sensing of the signals.

11. A method for delivering neurostimulation, the method comprising:
    delivering the neurostimulation from a stimulation device;
    receiving sensed signals from sensors and processing the sensed signals using a sensing circuit having adjustable settings controlling the processing of the sensed signals;
    controlling the delivery of the neurostimulation using the processed sensed signals using a control circuit; and
    controlling the settings of the sensing circuit for receiving the sensed signals from different sensors selected from the sensors for different times according to a precomposed sequence of sensing blocks using the control circuit, the precomposed sequence of sensing blocks each including a set of sensing parameters specifying a sensor to be used for sensing each signal of the sensed signals and a sampling frequency to be used for sensing the each signal, the set of sensing parameters programmable for each sensing block of the sequence of sensing blocks for adjusting the settings of the sensing circuit for that sensing block.

12. The method of claim 11, further comprising customizing the sequence of sensing blocks for at least one of a patient or a therapy.

13. The method of claim 12, wherein customizing the sequence of sensing blocks comprises customizing each of one or more blocks of the sequence of sensing blocks.

14. The method of claim 13, further comprising adjusting at least one sensing parameter of the set of sensing parameters according to at least one of a schedule or a specified event.

15. The method of claim 13, further comprising adjusting at least one sensing parameter of the set of sensing parameters using one or more signals of the processed sensed signals.

16. The method of claim 13, further comprising dynamically adjusting at least one sensing parameter of the set of sensing parameters during the delivery of the neurostimulation and the sensing of the signals.

17. The method of claim 11, wherein receiving the sensed signals from the sensors and processing the sensed signals using the sensing circuit comprises receiving and processing two or more signals of the sensed signals simultaneously using a plurality of individually controllable sensing channels of the sensing circuit.

18. The method of claim 11, further comprising storing one or more sensing algorithms in the control circuit, and wherein controlling the settings of the sensing circuit comprises executing a sensing algorithm selected from the stored one or more algorithms.

19. The method of claim 18, comprising executing the sensing algorithm using firmware of a microcontroller of the control circuit and storing the set of sensing parameters in the microcontroller and one or more registers coupled to the microcontroller to allow the settings of the sensing circuit to be adjusted without changing the firmware.

20. A non-transitory computer-readable storage medium including instructions, which when executed by a system, cause the system to perform a method for delivering neurostimulation, the method comprising:
 delivering the neurostimulation from a stimulation device;
 receiving sensed signals from sensors and processing the sensed signals using a sensing circuit having adjustable settings controlling the processing of the sensed signals;
 controlling the delivery of the neurostimulation using the processed sensed signals using a control circuit; and
 controlling the settings of the sensing circuit for receiving the sensed signals from different sensors selected from the sensors for different times according to a precomposed sequence of sensing blocks using the control circuit, the precomposed sequence of sensing blocks each including a set of sensing parameters specifying a sensor to be used for sensing each signal of the sensed signals and a sampling frequency to be used for sensing the each signal, the set of sensing parameters programmable for each sensing block of the sequence of sensing blocks for adjusting the settings of the sensing circuit for that sensing block.

* * * * *